(12) United States Patent
Justman et al.

(10) Patent No.: US 8,900,646 B2
(45) Date of Patent: Dec. 2, 2014

(54) COMPOSITION AND METHOD FOR MINIMIZING BULLING BEHAVIOR OF CATTLE

(71) Applicants: Danny Justman, Las Animas, CO (US); Melissa Justman, Las Animas, CO (US)

(72) Inventors: Danny Justman, Las Animas, CO (US); Melissa Justman, Las Animas, CO (US)

(*) Notice: Subject to any disclaimer, the term of this patent is extended or adjusted under 35 U.S.C. 154(b) by 0 days.

(21) Appl. No.: 13/736,064

(22) Filed: Jan. 7, 2013

(65) Prior Publication Data

US 2013/0209591 A1   Aug. 15, 2013

Related U.S. Application Data

(60) Provisional application No. 61/583,515, filed on Jan. 5, 2012.

(51) Int. Cl.
*A61K 36/81* (2006.01)
*A61K 36/61* (2006.01)
*A61K 36/00* (2006.01)

(52) U.S. Cl.
USPC ............ 424/760; 424/725; 424/747; 424/742

(58) Field of Classification Search
USPC .................. 424/760, 725, 747, 742
See application file for complete search history.

(56) References Cited

U.S. PATENT DOCUMENTS 5,983,839 A * 11/1999 O'Byrne et al. .............. 119/860
5,993,792 A * 11/1999 Rath et al. .................. 424/70.28

FOREIGN PATENT DOCUMENTS

GB      190324505 A  *  0/1904
JP      02005002040 A  *  1/2005

* cited by examiner

*Primary Examiner* — Patricia Leith
(74) *Attorney, Agent, or Firm* — Invention Protection Associates, LLC

(57) ABSTRACT

A method and composition for treating feedlot cattle in order to mask odor or pheromones given by cattle that trigger other cattle to mount them in a behavior pattern known as Buller Steer Syndrome, or to at least provide a scent which neutralizes that behavior.

9 Claims, No Drawings

COMPOSITION AND METHOD FOR MINIMIZING BULLING BEHAVIOR OF CATTLE

This non-provisional application claims the benefit of provisional application No. 61/585,515 filed Jan. 5, 2012.

BACKGROUND OF THE INVENTION

Buller Steer Syndrome (hereinafter, referred to as simply "BSS") is a behavioral disorder commonly exhibited by feedlot cattle. It is characterized by a tendency of some feedlot steers to mount the backs, or "bull," particular other steers on a persistent basis and not for any breeding or sexual purposes. In this dynamic, consistently dominant behaving steers are referred to as "riders," while consistently subordinate steers are called "bullers." Typically, in a feedlot pen containing several steers, a particular one or few buller steers are continually ridden by the same several rider steers. And although butlers usually do not aggressively resist being bulled, after enduring being ridden over prolonged periods of time, they become fatigued and often show significant outward symptoms of duress. At minimum, those symptoms can be in the form of bruising, abscesses and hair loss. At worst, bulling behavior leads to buller steer suffering movement loss, broken bones, stress-related illness and even death—any of which can result in a steer's meat yield potential being greatly diminished, if not entirely lost. Consequently, BSS represents a significant negative economic impact to feedlot ranchers, and it, along with bovine respiratory disease and footrot, is one of the top three health concerns in the cattle feeding industry.

It has been estimated that bulling behavior renders a loss of between $25 and $70 per buller steer to the feedlot industry. Reflected in that range of figures are the incremental costs of providing labor and facilities to segregate butlers and riders in separate pens, as well as weight loss and other forms of yield degradation. Therefore, ranchers and researchers alike have continually endeavored to identify both the underlying cause(s) of BSS and effective ways to combat it. As for causation, although nothing has been definitively proven scientifically, varying levels of consensus have formed around notions of BSS being triggered by the following factors related to feedlot cattle: pheromones; odors (of steers generally and of their urine); estrogen level; testosterone level; breed type; body size; age; hair coloration; horn status; feed substances; place of raising; social hierarchy; weather; and pen size/density. In particular, considerable credence has been given to the idea that butlers release odors or pheromones that entice other steer to ride them.

Since there is no known "cure" or even foolproof way of predicting bulling behavior among a random set of steers, surveilling bulling activity and then responsively managing the behavior is a substantial responsibility of feedlot operators. Heretofore, well-recognized methods of managing bulling behavior virtually all involved physically segregating identified bullers from riders and other non-bullers—either by placing them in altogether separate holding pens or by integrating overhead barriers and other partitions into pen structures for the purpose of making the act of mounting physically untenable. Of course, as previously mentioned, that management activity comes at a labor and facility cost. Furthermore, placing bullers in their own separate buller pen is only marginally effective due to the fact that some previously buller steers then begin displaying bulling behavior toward other steers within the buller pen environment. In fact, the present inventors have observed that confining butlers exclusively to buller pens has about a 30% rate of success (i.e., approximately only 30% of isolated butlers ultimately escape negative impacts of bulling and reach their full yield potential). And the cost and ineffectiveness of present buller isolation methods proportionately increases with increased steer count, as it has been observed that the greater the number of steers confined within a single pen or control area, the greater incidence of butlers there tends to be. That, in turn, may necessitate the existence of more separate pen areas for separately housing steers identified as butlers initially and so-identified after a round(s) of segregation.

Thus, there is an outstanding need to inhibit bulling behavior in a manner that is more outcome and cost effective than is the conventional practice of erecting partitions to segregate cattle. The present inventors have observed that the compound described herein and methods for its use substantially fulfill this need.

SUMMARY OF THE INVENTION

The present invention generally relates to ways of minimizing bulling behavior commonly exhibited by feedlot cattle, and it specifically relates to a treatment composition and use method for masking the odor of or pheromones secreted by would-be subordinate cattle in bulling activity and/or for otherwise repulsing would-be dominant cattle to the extent that their appetite for engaging in bulling behavior is lost, yet they are still able to coexist within a pen environment without the would-be butler or non-buller cattle experiencing undue stress or trauma.

In its broadest sense, the present inventive method combines the notions of: (1) identifying cattle which are likely to attract others to persistently mount them (preferably, prior to that activity ever commencing) and (2) applying to the attracting cattle a non-toxic, topical compound which is not absorbed into the bloodstream (and, therefore, does not affect consumability of their beef) and effectively either: (a) dominates and masks pheromones or other odors secreted by them which may trigger bulling behavior; or (b) at least creates a competing odor that sufficiently inhibits other cattle from bulling them, hut does not so offend other cattle as to make their coexistence in a single pen or control area untenable.

It is, therefore, an object of the present invention to provide a method for minimizing bulling behavior among cattle that does not necessitate isolating or otherwise erecting physical barriers around them for the specific purpose of inhibiting that behavior—and thereby enables feedlot operators to avoid incurring the operational costs of employing separation/partition strategies. In one aspect of the invention, a feedlot manager, rather than wait to observe bulling behavior and reacting with conventional isolation techniques, should, to the extent possible, preemptively identify factors which are widely considered indicative of potential for subordinate disposition within a cattle pen. For example, although it is unclear as to whether higher levels of serum and urinary estrogen and testosterone are causative of or are reactions to butler status, a feedlot manager would be well-advised to test their steers to determine which ones have elevated hormone levels, and then presume that those particular steers at at-risk for becoming bullers (before they have had the opportunity to actually demonstrate that behavior). Alternatively, other visually perceptible steer characteristics, such as body size, hair coloration or horn status or other knowable facts, such as breed type or place of raising (which can be instructive to the extent that there is a known relatively high incidence of butlers emanating from a particular ranch or location of early development) should be used as predictors of buller status.

Then, in another aspect of the invention, the predicted bullers (as well as proven bullers) are treated with a topical formula that the present inventors have observed to be statistically effective in, at minimum, neutralizing would-be dominant steers from engaging in bulling behavior by way of arming would-be subordinate steers with an offending odor that wards off rider steers. And that treatment, quite possibly, is effective in masking the detectability of odors and pheromones that may trigger bulling behavior.

Accordingly, it is another object of the present invention to provide a particular buller-prevention treatment mixture that has demonstrated effectiveness in minimizing the occurrence of bulling behavior in control areas in which a large number of steers are confined without any attempt at buller-rider separation having been made.

Nevertheless, it is also an object of the present invention to introduce to the feedlot industry the concept of treating buller steers with any topically applied composition that inhibits bulling behavior and obviates the need to physically isolate butler steers from their dominant counterparts.

DETAILED DESCRIPTION OF THE PREFERRED EMBODIMENTS

This disclosure, as defined by the claims that follow, generally relates to applying odor-masking, or otherwise behavior-modifying, mixtures to the backs of cattle topically for the explicit purpose of inhibiting bulling behavior within a feedlot pen. More specifically, the invention is drawn to a mixture that, in one embodiment, combines: capsicum, peppermint oil, eucalyptus oil, vegetable oil, glycerin, xantham gum, sodium bicarbonate and water. In another embodiment, the mixture additionally includes an essential oil such as rosemary cineole oil or cajeput oil. However, experimental observation has indicated that even other ingredients may be introduced, and a few behaviorally effective equivalent components may be substituted for those listed.

Furthermore, by "vegetable oil," it is contemplated that any number of plant extracted oils such as soybean oil, canola oil, olive oil, sesame oil, almond oil, sunflower oil, safflower oil, peanut oil, cottonseed oil, coconut oil, palm oil, rice bran oil, or any combination thereof may be employed. It should also be noted that capsicum can be utilized in oil or powder form. Nevertheless, the peppermint oil, eucalyptus oil and capsicum are the mixture's active ingredients in that they provide bulling behavior modifying scent properties.

In the aforementioned embodiment, the mixture includes, by approximate volume percentage, 0.8% capsicum, 0.3% peppermint oil, 0.8% eucalyptus oil, 8.3% vegetable oil, 5% glycerin, 0.1% xantham gum, 10% sodium bicarbonate, and the remainder being water. In this, or any other suitable embodiment, the composition can be produced in any volumes as a proportional mixture—meaning that the production batch can be scaled up or down as desired. However, it should be emphasized that aforelisted volume percentages are approximations and can range moderately. In fact, exact proportions can be modified (and substitute components introduced) in order to change the form of the output mixture, as the composition can be effectively presented as a powder, oil, liquid, gel or any combination thereof. For example, a greater or lesser proportion of xantham gum can be used to thicken or more liquefy the texture of the mixture.

Finally, the mixture may be applied along steers' backs according to any suitable application procedure. It may be poured, sprayed, rubbed on or adhered via tape or a patch that is impregnated or otherwise possesses the present mixture.

It is understood that substitutions and equivalents for and combinations of various elements set forth above may be obvious to those skilled in the art and may not represent a departure from the spirit of the invention. Therefore, the full scope and definition of the present invention is to be set forth by the claims that follow.

What is claimed is:

1. A method for minimizing bulling behavior of cattle confined to a control area, the method comprising:
   identifying cattle, within the control area, exhibiting bulling behavior; and
   applying a topical composition to the hide of the so identified cattle, wherein said composition comprises a mixture of: capsicum, peppermint oil, eucalyptus oil, vegetable oil, glycerin, xantham gum, sodium bicarbonate and water.

2. The method of claim 1, wherein said bulling behavior is characterized by being persistently mounted by other cattle.

3. The method of claim 1, wherein said composition is applied along the back areas of said identified cattle.

4. The method of claim 1, wherein said composition is a spray, cream, gel, paste, powder, oil, or liquid.

5. The method of claim 1, wherein the volume percentages of components of said composition are as follows: capsicum 0.8%, peppermint oil 0.3%, eucalyptus oil 0.8%, vegetable oil 8.3%, glycerin 5%, xantham gum 0.1%, sodium bicarbonate 10%, and water the remainder.

6. The method of claim 1, wherein said capsicum is an oil or powder.

7. The method of claim 1, wherein said peppermint oil, eucalyptus oil and capsicum are active ingredients.

8. The method of claim 1, wherein said composition further comprises rosemary cineole oil.

9. The method of claim 1, wherein said composition further comprises cajeput oil.

* * * * *